United States Patent [19]

Sonntag et al.

[11] 4,073,926
[45] Feb. 14, 1978

[54] MONO-QUATERNARY AMMONIUM SALTS OF HYDANTOIN AND COMPOSITIONS THEREOF

[75] Inventors: Norman O. V. Sonntag, Montoursville; John Douglas Freilich, S. Williamsport, both of Pa.

[73] Assignee: Glyco Chemicals, Inc., Greenwich, Conn.

[21] Appl. No.: 729,343

[22] Filed: Oct. 4, 1976

[51] Int. Cl.² .................. A61K 31/415; C07D 233/72
[52] U.S. Cl. ............................ 424/273 R; 106/15 R; 210/64; 252/8.55 D; 252/49.5; 252/106; 252/107; 252/401; 548/312
[58] Field of Search ...................... 260/309.5; 424/273

[56] References Cited

U.S. PATENT DOCUMENTS

| | | | |
|---|---|---|---|
| 2,591,103 | 4/1952 | Spurlock | 260/309.5 |
| 2,886,487 | 5/1959 | Kupferberg et al. | 260/309.5 |
| 3,641,248 | 2/1972 | Adolphi et al. | 260/309.5 |
| 3,681,377 | 8/1972 | Singhal | 260/309.5 |
| 3,716,552 | 2/1973 | Fujinami et al. | 260/309.5 |
| 3,835,151 | 9/1974 | Havera et al. | 260/309.5 |
| 3,843,677 | 10/1974 | Cleveland | 260/309.5 |
| 3,892,748 | 7/1975 | Hayao et al. | 260/309.5 |

OTHER PUBLICATIONS

Joshi et al., Chem. Abst., 1973, vol. 78, No. 92406y.
Ozawa et al., Chem. Abst., 1968, vol. 69, No. 66886z.
Kawahara, Chem. Abst., 1963, vol. 58, Columns 6921–6922.

*Primary Examiner*—Natalie Trousof
*Attorney, Agent, or Firm*—Cushman, Darby & Cushman

[57] ABSTRACT

Described herein are mono-quaternary ammonium salts of hydantoin having the formula:

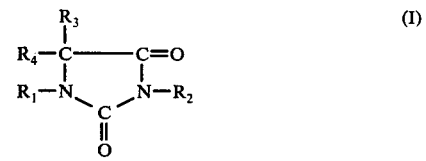

(I)

wherein:
one of $R_1$ and $R_2$ is hydrogen or lower alkyl of 1 to 6 carbons and the other is

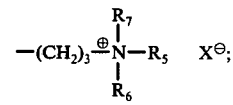

$R_3$ and $R_4$, which may be the same or different, are selected from the group consisting of hydrogen, alkyl of 1 to 6 carbons, phenyl or taken together $R_3$ and $R_4$ may be a cycloaliphatic group of 4 or 5 carbon atoms;
$R_5$, $R_6$ and $R_7$, which may be the same or different, are selected from the group consisting of benzyl or —$C_pH_{2p+1}$;
X is a halide or sulfate anion; and
p is an integer from 1 to 24.

The salts are useful anti-static agents. A number of the salts possess broad spectrum fungicidal and/or bactericidal activity and, accordingly, compositions having such activity contain as an active ingredient certain mono-quaternary ammonium salts of hydantoin.

13 Claims, No Drawings

MONO-QUATERNARY AMMONIUM SALTS OF HYDANTOIN AND COMPOSITIONS THEREOF

BACKGROUND OF THE INVENTION

This invention relates to a new class of hydantoin derivatives which are characterized as salts having linked to either one of the ring nitrogens a quaternary ammonium group. The mono-quaternary ammonium salts of hydantoin, according to the present invention, are useful as anti-static agents. Certain of these mono-quaternary ammonium hydantoin salts exhibit bactericidal and/or fungicidal activity, and to that extent, this invention relates to germicidal compositions having a broad spectrum of bactericidal and fungicidal activity and containing as an active ingredient certain mono-quaternary ammonium salts of hydantoins, and to methods for combating bacteria and fungi.

The survival of man has for a long time considerably depended upon his ability to protect both himself and the environment upon which he depends from the various agents which tend to destroy them. With an ever-increasing world population, there is an important and continuing need to improve the efficiency of both the methods and substances which provide protection from undesirable bacteria and fungi. Such improvements may take the form of more effective control of bacteria and/or fungi by using less material or labor. Certain of the compounds, compositions and methods of the present invention provide a major step forward in both of these areas.

As noted in U.S. Pat. No. 3,228,829, water-containing organic mixtures, such as emulsified cutting oils, latexes, latex paints, aqueous adhesives, hydraulic fluids, and pulp dispersions used in paper-making, in the absence of an effective germicide, are characteristically subject to attack by putrefactive bacteria, particularly, species of Pseudomonas and Aerobacter which cause loss of useful properties, foul odors, slime formation and the possibility of skin infections in persons handling these materials. The problems involved in preserving water-containing systems against microbial decomposition are many and varied and a very considerable amount of work has been done in efforts to find protective substances which meet the numerous requirements. The variety of materials offered for the purpose is, to some extent, evidence that none is without disadvantage.

The first requisite of such a preservative is, of course, its activity and effectiveness against the offending organisms. Contributing to the effectiveness of a preservative are its stability and its persistence in the system. To exert its activity in these sytems, the preservative must have a degree of water solubility. Where the aqueous system is subject to handling, the preservative should be non-irritating to the skin under the conditions of use. For reasons of waste disposal, it is becoming increasingly important that the toxicity of these preservative materials to humans and fish be relatively low.

Furthermore, with the significant restrictions which have been placed upon the use of such bactericides as hexachlorophene, the present invention provides a promising alternative.

Accordingly, it is the primary object of the present invention to provide new broad spectrum bactericidal and fungicidal compositions incorporating therein lower effective amounts of active ingredients than generally employed heretofore.

Also, it is a further object of the present invention to provide a new group of hydantoin compounds which exhibit anti-static properties.

Still yet another object of the present invention is to provide a new class of compounds having specialty surfactant properties.

These and other objects of the present invention will be apparent from the following description.

SUMMARY OF THE INVENTION

The mono-quaternary ammonium salts of hydantoin, according to the present invention, are represented by the following structural formula:

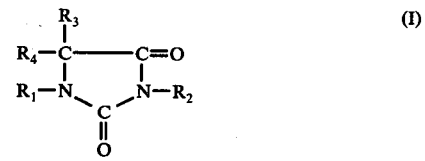

wherein:
one of $R_1$ and $R_2$ is hydrogen or lower alkyl of 1 to 6 carbons and the other is

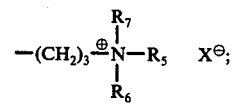

$R_3$ and $R_4$, which may be the same or different, are selected from the group consisting of hydrogen, alkyl of 1 to 6 carbons, phenyl or taken together may be a cycloaliphatic group of 4 or 5 carbon atoms;

$R_5$, $R_6$ and $R_7$, which may be the same or different, are selected from the group consisting of benzyl or $-C_pH_{2p+1}$;

X is a physiologically acceptable anion; and
p is an integer from 1 to 24.

Preferred hydantoin derivatives of the present invention are the mono-quaternary ammonium salts of 5,5-disubstituted hydantoin wherein:

$R_3$ and $R_4$, which may be the same or different, are selected from the group consisting of alkyl of 1 to 6 carbons, phenyl or taken together $R_3$ and $R_4$ may be a cycloaliphatic group of 4 or 5 carbon atoms. Especially preferred are the 5,5-dimethyl hydantoin derivatives.

Preferably, $R_7$ is $-C_pH_{2p+1}$ wherein p is an integer from 8 to 24 and most preferably 12 to 18, while $R_5$ and $R_6$ are lower alkyl of 1 to 6 carbons, particularly methyl. Examples of such compounds according to the present invention include those having the formula:

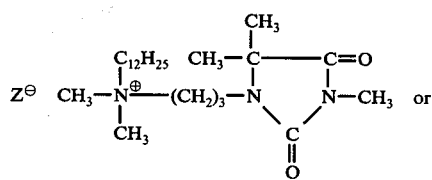

-continued

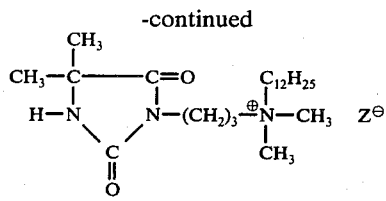

wherein Z is a physiologically acceptable anion.

These salts exhibit anti-static properties and may be incorporated, for example, into textile materials, such as carpets, socks and undergarments, during the finishing thereof to impart anti-static and softening properties thereto. The salts also possess surfactant properties and are useful wetting agents.

Also, according to the present invention, the incorporation of certain mono-quaternary ammonium salts of hydantoin in aqueous organic mixtures, cosmetic compositions, as well as application of these salts to the skin, provides effective germicidal protection and considerably reduces or precludes damage to the compositions or skin due to microbial attack of bacteria or fungi. Bacterial and fungal infestations and infections may be destroyed or prevented from increasing to prohibitive levels by the presence of at least one active compound according to the present invention. Thus, certain of the compounds, according to the present invention, are germicidal having broad spectrum bactericidal/fungicidal activity.

Compounds, according to the present invention, which having been found to possess bactericidal and/or fungicidal properties, are those having the formula:

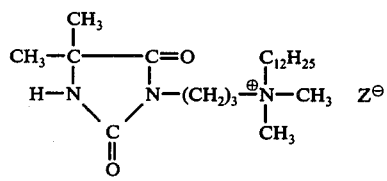 (II)

wherein Z is a physiologically acceptable anion.

Suitable physiologically acceptable anions include the halogens, particularly bromide, chloride or iodide, as well as sulfate. The halogens are preferred, especially bromide.

It is to be understood that when sulfate anions are present in the compounds of the present invention, only one half mole of anion is present for each mole of cation.

Representative of but a few of the many mono-quaternary ammonium salts of 3-(3'-aminopropyl) hydantoin compounds encompassed by the present invention, there may be mentioned:

N,N-dimethyl-N-dodecyl quaternary ammonium bromide salt

N,N-dimethyl-N-dodecyl quaternary ammonium chloride salt

N,N-dimethyl-N-benzyl quaternary ammonium chloride salt

N,N-dimethyl-N-dodecyl quaternary ammonium iodide salt

N-methyl-N-ethyl-N-dodecyl quaternary ammonium bromide salt

N-methyl-N-ethyl-N-dodecyl quaternary ammonium chloride salt

N-methyl-N-benzyl-N-dodecyl quaternary ammonium bromide salt

N,N-dibenzyl-N-dodecyl quaternary ammonium bromide salt

N,N-dimethyl-N-octadecyl quaternary ammonium bromide salt

N,N-dimethyl-N-hexadecyl quaternary ammonium chloride salt

N,N-dimethyl-N-hexadecyl quaternary ammonium bromide salt

One may also envision similar mono-quaternary ammonium salts derived from 1-(3'-aminopropyl) hydantoins, and to that end, the above quaternary salts are included as representative of but a few.

These salts are but a few of the many compounds according to the present invention and are intended as representative of the hydantoin, 5-monosubstituted- and 5,5-disubstituted derivatives; including but not limited to hydantoin, 5-methyl hydantoin or 5,5-dimethyl hydantoin.

While the 5,5-disubstituted hydantoin compounds are preferred, particularly the 5,5-dimethyl, other disubstituted materials may also be used to form any of the above salts. For example, 5-methyl-5-ethyl hydantoin, 5,5-diphenyl hydantoin, 5-methyl-5-phenyl hydantoin, and 5,5-pentamethylene hydantoin are suitable.

As will be appreciated, this specification sets forth a considerable number of mono-quaternary ammonium salts of hydantoin and their method of preparation. For the skilled man in the art, it is only a matter of elementary chemistry and relative ease to prepare a particular derivative differing from any compound not specifically set forth in this specification merely in the number of carbon atoms in any alkyl or aromatic moiety. All that need be done is to commence with the appropriate reactants and, if necessary, adjust the reaction conditions. Hence, it is impractical to recite herein specifically each and every simple variation possible.

The compounds of (I) and (II) can be readily prepared by the addition of 1 mole of acrylonitrile to the applicable hydantoin (which may be mono- or di-substituted, or unsubstituted at the 5-position, e.g., 5,5-dimethyl hydantoin) so as to produce the corresponding mono-nitrile. The reaction is carried out in a confined reaction zone (e.g., a stirred autoclave) in an aqueous media and in the presence of a catalytically effective amount (e.g., about 0.5 to 1.5%, by weight of starting hydantoin) of a 45–50% aqueous solution of KOH or NaOH at a temperature ranging from about 70° to 101° C, represented schematically as follows:

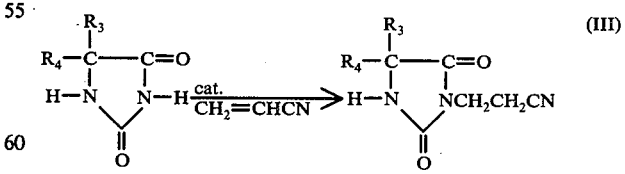 (III)

The nitrile (III) produced is reduced with hydrogen under a pressure of 400–600 p.s.i. at a temperature of about 100° to 125° C in the presence of a suitable catalyst (e.g., Raney Nickel) to produce the corresponding mono-amine (IV) represented schematically as follows:

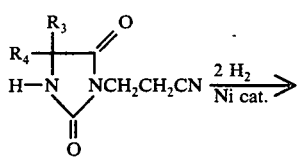 (III)

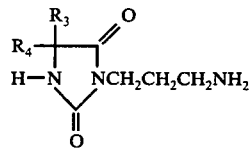 (IV)

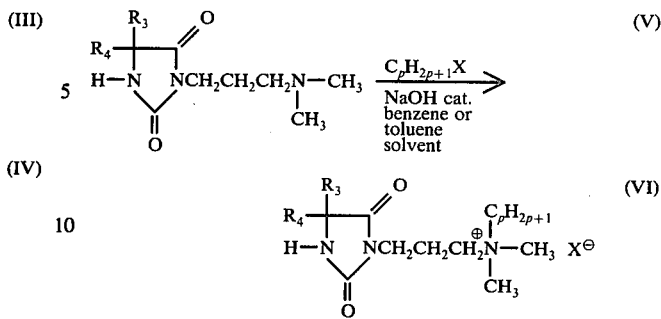 (V)

(VI)

The mono-amine (IV) is then methylated using formaldehyde and formic acid to produce the corresponding mono-tertiary amine (V) represented schematically as follows:

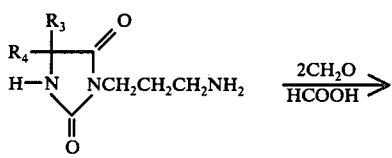 (IV)

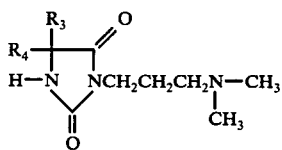 (V)

Other useful mono-tertiary amines may be prepared by stepwise alkylation of the mono-amine (IV). For example, the N-methyl-N-benzyl-tertiary amine (Va) may be prepared by stepwise addition of methyl chloride followed by benzyl chloride to the amine IV represented schematically as follows:

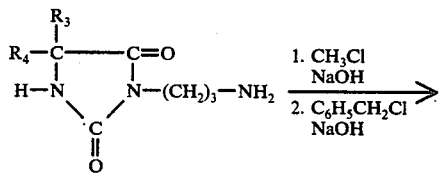 (IV)

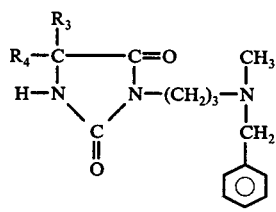 (Va)

Compounds wherein $R_5$ and/or $R_6$ are $—C_pH_{2p+1}$ may be prepared in similar fashion by stepwise addition of the appropriate alkyl halide $C_pH_{2p+1}X$ (where X and p are defined as above).

Reaction of the tertiary amine (V) or (Va) with an appropriate alkyl halide (e.g., dodecyl bromide) of the formula $C_pH_{2p}X$ (X and p being defined above) preferably in the presence of an effective amount (e.g., less than 1%) of alkali metal hydroxide catalyst and solvent yields the desired monoquaternary ammonium salt (VI) represented schematically as follows:

It is recognized that commercially available alkyl halides of the formula $C_pH_{2p+1}X$ may be mixtures which vary, for example, according to chain length, and as such these mixtures are as suitable for the present invention as the alkyl halide in its purified state. For example, a suitable alkyl halide would include a mixture of predominantly octadecyl halide together with hexadecyl halide and/or tetradecyl halide. Compounds prepared from such mixtures, of course, may contain alkyl chain length which vary within the desired range.

Suitable hydantoins used as starting materials in the preparation of (I) and/or (II) include hydantoin, 5-methyl hydantoin, 5,5-dimethyl hydantoin, 1,5,5-trimethyl hydantoin and 3,5,5-trimethyl hydantoin.

It is to be noted that the addition of the first mole of acrylonitrile in alkaline media to hydantoins which possess unsubstituted nitrogen atoms at the 1- and 3-position takes place at the 3-position. Therefore, in preparation of the compounds having a mono-quaternary ammonium substituent at the 1-position nitrogen and hydrogen on the 3-position nitrogen, it is necessary to add a protecting group, inert to acrylonitrile, to the 3-position prior to the addition of acrylonitrile, which group is subsequently removed. One may envision, for example, the addition of a $—CH_2Cl$ substituent to the 3-position nitrogen (via treatment with formaldehyde and thionyl chloride) which may be removed by hydrolysis subsequent to the addition of the acrylonitrile.

In a further aspect of the present invention, there is provided a bactericidal composition comprising as an active ingredient, a bactericidally effective amount of a quaternary ammonium salt of hydantoin as represented in formula (II) above.

A yet further aspect of the present invention provides a fungicidal composition comprising as an active ingredient a fungicidally effective amount of a quaternary ammonium salt of hydantoin as represented by formula (II) above.

Thus, the invention provides for germicidal compositions having broad spectrum bactericidal/fungicidal activity and containing a hydantoin of the above formula (II) in an effective amount as an active ingredient to combat bacteria and fungi simultaneously in cases of dual infestation.

While the compounds (I) of the present invention are useful as anti-static agents, surfactants or wetting agents, certain of these, i.e., the compounds (II), are particularly suited for use with and incorporated in a bactericidally and/or fungicidally effective amount in deodorants, soaps, cosmetics, antiseptic lotions and the like to combat, destroy and/or prevent the infestation of undesired bacteria, fungi, or both. The compounds may be used to combat and prevent undesired bactericidal and fungicidal infections in the skin wounds of animals, including man, by applying to the locus of the skin wound a bactericidally and/or fungicidally effective amount of the active compound as a wound cleaner.

The active compounds (II) are well suited for addition to such aqueous organic mixtures as emulsified cutting oils, latexes, paints and the like to combat and prevent infestation of putrefactive bacteria as described in the U.S. Pat. No. 3,228,829, which is incorporated herein by reference.

The broad spectrum bactericidal and/or fungicidal compositions, according to the present invention, in addition to an effective amount of the active compound (II) comprise an inert solid or liquid diluent or carrier. Generally, the active compound is effective when present in an amount of from about 0.0025 to about 10%, and preferably 0.0025 to about 0.1% by weight, and may be effectively incorporated into such aqueous-organic mixtures as described in the above-mentioned U.S. Pat. No. 3,228,829.

Thus, the bactericidal and/or fungicidal compositions may be prepared in the form of liquids or solids. The active compound may, for example, be incorporated directly into cosmetic compositions to combat and prevent infestation of undesirable bacteria and/or fungi. The active compound may be present in solution, suspension or antiseptic formulation.

The compounds (II) may be incorporated in an effective amount in formulations in the nature of gels, creams, lotions or powders.

The compositions, when in the form of a liquid, preferably contain a surface-active agent so as to effect dispersion of the active compound (II) in aqueous solutions. These solutions may be used, for example, as sprays.

The bactericidal and/or fungicidal compositions, when used as an antiseptic to combat, destroy or prevent infestation of undesirable bacteria, fungi, or both, necessitate that the inert carrier be non-toxic. Such compositions may be in the form of gels, creams, lotions, suspensions, and powder which may be prepared in a conventional manner by incorporation of the active compound therein as described in U.S. Pat. No. 2,886,487, which is incorporated herein by reference.

As noted, the bactericidal and/or fungicidal compositions of the invention may be used in a number of ways.

The compositions may be used as sprays in the form of aerosols wherein the formulation is held in a container under pressure in the presence of a propellant, such as fluorotrichloromethane or dichlorodifluoromethane.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water in order to form aqueous preparations which remain homogeneous for a relatively long period of time.

It is to be understood that the fungicidal compositions of this invention may comprise, in addition to the hydantoin salt, one or more other compounds having biological activity.

The following examples are provided to more fully illustrate the invention, but are not to be construed as limiting the scope thereof.

EXAMPLE 1

Preparation of Mono-Quaternary Ammonium Salt (VII)

To a 22 liter flask fitted with stirrer, condenser and thermometer is added 3203 g (25 mol) DMH and 5000 ml $H_2O$. Upon heating to 73° C, complete solution of the DMH results Then 664 g (12.5 mol) acrylonitrile and 24 g of 50% aq. NaOH catalyst is added. Refluxing is begun, and the solution is maintained at reflux until the temperature reaches ~100° C. All heating is now stopped, and when the temperature falls to 73° C, the remaining 663 g (12.5 mol) acrylonitrile is charged. Refluxing is started once again. When the temperature reaches 100°–101° C, all heating is stopped, external cooling is applied until the temperature reaches ~31° C, and a seed crystal of mononitrile is added to the cooled reaction solution. The mononitrile crystallizes out of solution and is collected via filtration and air dried: mp 97.5°–99.5° C (lit. 98°–101° C), glc (TMS derivative) = 99%, yield = 3,245 g (71.6%).

To a 2 liter Parr pressure reaction vessel is added 370.4 g (2 mol) mononitrile, 41.2 g Raney Nickel catalyst and 500 ml toluene. The system is flushed with $H_2$, and then a partial pressure of 70 p.s.i. $NH_3$ is added. The system is then pressurized with $H_2$ to 500 p.s.i. The temperature is raised to 117° C and the $H_2$ uptake is recorded, while continually maintaining the pressure at 400–600 p.s.i. Once the $H_2$ uptake is complete, the reactor is cooled and the toluene solution is filtered to remove nickel catalyst. Upon standing, the toluene filtrate yields white or very pale blue crystalline pure monoamine: mp = 79-81° C (lit. ~70° C), total amine value (TAV) = 297.9/300 = 98.4%, yield = 90-95%.

A modified Eschweiler-Clarke reaction is used to prepare the mono-tert-amine. To a 1 liter flask fitted with condenser, stirrer and thermometer is added 175.6 g (0.943 mol) monoamine and 153.9 g 37% aq. formaldehyde. After cooling to 25° C, 109.5 g. 90% formic acid is added, resulting in vigourous gas evolution. After 5 minutes, a final 109.5 g 90% formic acid is added. The mixture is heated to 105° C and refluxed for 6 hours. After cooling, the pH of the solution is adjusted to 7.21 with 50% aq. NaOH. The now neutralized solution is concentrated on the roto-evaporator, yielding a gummy solid. Isopropyl alcohol is added to the solid, which dissolves the desired mono-tert-amine leaving the sodium formate by-product for collection via filtration and subsequent discarding. The filtrate is concentrated on the rotoevaporator, yielding greenish crude mono-tert-amine. Distillation of the crude amine under reduced pressure yields pure light yellow, clear, slightly viscous mono-tert-amine: BP 143°–148° C/250 μ, glc (BSA derivative) = 99+%, yield = 100 ml (52.6%).

To a 500 ml flask fitted with stirrer, condenser and thermometer is added 43.0 g (0.2 mol) mono-tert-amine, 71.4 g (0.28 mol) bromododecane and 250 ml benzene. Some quaternary salt precipitates out of solution almost immediately. The stirred mixture is heated to 85° C, when 1 drop 50% aq. NaOH is added as a catalyst. The mixture is then refluxed for 8 hours, yielding a hazy viscous solution. Upon cooling and standing, a viscous semi-solid precipitates from solution. By treating the mixture with $Et_2O$, distinct waxy white solid mono-dodecyl bromide quaternary salt is obtained, which is collected via filtration, washed with solvent and dried in the vacuum oven: mp 85°–88° C, positive halogen test with AgNO₃, very hygroscopic, yield = 50 g (54%), as represented by the formula:

$$\begin{array}{c} CH_3 \\ | \\ CH_3-C———C=O \quad C_{12}H_{25} \\ | \quad\quad\quad | \quad\quad\quad\quad \oplus| \\ H-N \quad N-(CH_2)_3-N-CH_3 \quad Br^{\ominus} \\ \diagdown C \diagup \quad\quad\quad\quad | \\ \| \quad\quad\quad\quad\quad\quad\quad CH_3 \\ O \end{array}$$ (VII)

C, H, N, Br analysis: Found: C 57.02 H 9.56 N 9.02 Br 17.44 Theory: C 57.13 H 9.59 N 9.09 Br 17.28 IR Spectrum (solid film) = 3.17, 3.42, 3.5, 5.67, 5.85, 6.81, 6.92, 7.04, 7.35, 7.87, 9.39, 12.99 μ

EXAMPLE 2

Preparation of Monobenzyl Quaternary Salt (VIII)

To a 500 ml flask fitted with condenser, stirrer and thermometer is added 43.3 g (0.20 mol) mono-tert-amine from Example 1, 36.2 g (0.28 mol) benzyl chloride and 250 ml benzene. The mixture is stirred vigorously and heated at reflux for 3 hours. A white precipitate forms, which is collected via filtration, washed with solvent and dried in a vacuum oven. If desired, the monobenzyl chloride quaternary salt may be recrystallized from a mixture of isopropanol, ethyl ether and water to yield 50 g (73.5%) of a white solid having mp 243°–244° C and the following structure and properties:

$$\begin{array}{c} CH_3 \quad\quad\quad\quad\quad\quad\quad C_6H_5 \\ | \quad\quad\quad\quad\quad\quad\quad\quad | \\ CH_3-C———C=O \quad CH_2 \\ | \quad\quad\quad\quad | \quad\quad\quad\quad \oplus | \\ H-N \quad N-(CH_2)_3-N-CH_3 \quad Cl^{\ominus} \\ \diagdown C \diagup \quad\quad\quad\quad | \\ \| \quad\quad\quad\quad\quad\quad\quad CH_3 \\ O \end{array}$$ (VIII)

C, H, N, Cl analysis: Found C 59.95 H 7.63 N 12.46 Cl 10.28 Theory: C 60.08 H 7.71 N 12.36 Cl 10.43

The quaternary ammonium salts produced in the Examples are water soluble.

The product compound of the Example 1 was tested for anti-bacterial and anti-fungal activity and compared to the known commercial broad spectrum bactericide/-fungicide, according to the following procedure.

Samples of the compound were prepared for testing by making a stock solution in sterile distilled water containing 10,000 parts per million. Serial dilutions of each sample were prepared in appropriate culture media which were then innoculated with the test cultures and incubated. The tests employing bacteria were performed in BBL Trypticase Soy Broth incubated for 48 hours at 35° C. The tests employing A. niger were performed in Difco Sabouraud Dextrose Broth incubated for 5 days at 26° C.

The test cultures were *Staphylococcus aureus* No. 6538, *Pseudomonas aeruginosa* No. 9027 and *Aspergillus niger* No. 16404. The results are set forth in Table 1 below.

TABLE I

| Active Compound Example | Concentration in parts per million | Test Culture and Results | | |
|---|---|---|---|---|
| | | Staphyloccus aureus # 6538 | Pseudomonas aeruginosa # 9027 | Aspergillis niger # 16404 |
| Compound VII (Example 1) | 1000 | 0 | 0 | 0 |
| | 900 | 0 | 0 | 0 |
| | 800 | 0 | 0 | 0 |
| | 700 | 0 | 0 | 0 |
| | 600 | 0 | 0 | 0 |
| | 500 | 0 | + | 0 |
| | 400 | 0 | + | 0 |
| | 300 | 0 | + | 0 |
| | 200 | 0 | + | + |
| | 100 | 0 | + | + |
| | 50 | 0 | — | — |
| | 25 | 0 | — | — |
| | 12.5 | + | — | — |
| | 6.25 | + | — | — |
| | 3.12 | + | — | — |
| | 1.56 | + | — | — |
| Comparative Sample* | 1000 | 0 | 0 | 0 |
| | 900 | 0 | 0 | 0 |
| | 800 | 0 | + | 0 |
| | 700 | 0 | + | + |
| | 600 | 0 | + | + |
| | 500 | 0 | + | + |
| | 400 | 0 | + | + |
| | 300 | 0 | + | + |
| | 200 | 0 | + | + |
| | 100 | + | + | + |

— Denotes no test.
+ Denotes growth.
0 Denotes no growth.
*Dowicil 200 is a 1-(3-chloroallyl)-3,5,7-triaza-1-azonia adamantene chloride available from Dow Chemical Company (see U.S. Pat. No. 3,228,829).

The minimum inhibitory concentrations are set forth in Table II below.

TABLE II

| | Minimum Inhibitory Centration (ppm) | |
|---|---|---|
| Test Culture | Example 1 | Dowicil 200* |
| Staph. aureus # 6538 | 25 | 200 |
| Pseudo. aerugin # 9027 | 600 | 900 |
| Asperg. niger # 16404 | 300 | 800 |

*Dowicil 200 is a 1-(3-chloroallyl)-3,5,7-triaza-1-azonia adamantane chloride available from Dow Chemical Company (see U.S. Pat. No. 3,228,829).

The invention in its broader aspects is not limited to the specific details shown and described, but departures may be made from such details within the scope of the accompanying claims without departing from the principles of the invention.

The invention may furthermore comprise, consist or consist essentially of the hereinbefore recited materials and steps.

What is claimed is:

1. A hydantoin derivative having the formula:

$$\begin{array}{c} R_3 \\ | \\ R_4-C———C=O \\ | \quad\quad\quad\quad | \\ R_1-N \quad\quad N-R_2 \\ \diagdown C \diagup \\ \| \\ O \end{array}$$

wherein:
one of $R_1$ and $R_2$ is hydrogen or alkyl of 1 to 6 carbon atoms and the other is

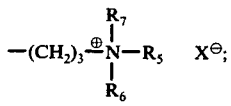

R$_3$ and R$_4$, which may be the same or different, are selected from the group consisting of hydrogen, alkyl of 1 to 6 carbons, phenyl or taken together R$_3$ and R$_4$ may be a cycloaliphatic group of 4 or 5 carbon atoms;

R$_5$, R$_6$ and R$_7$, which may be the same or different, are a group selected from the group consisting of benzyl or —C$_p$H$_{2p+1}$;

X is a physiologically acceptable anion;

p is an integer from 1 to 24.

2. A compound according to claim 1 wherein R$_3$ and R$_4$ are both methyl.

3. A compound according to claim 1 wherein:

R$_3$ and R$_4$, which may be the same or different, are selected from the group consisting of alkyl of 1 to 6 carbons, phenyl or taken together R$_3$ and R$_4$ may be a cycloaliphatic group of 4 or 5 carbon atoms.

4. A compound according to claim 1 wherein R$_5$ and R$_6$, which may be the same or different, are lower alkyl of 1 to 6 carbon atoms and r$_7$ is —C$_n$h$_{2n+1}$ wherein n is an integer from 8 to 24.

5. A compound according to Claim 4 wherein X is bromine, R$_5$ and R$_6$ are methyl and n is from 12 to 18.

6. A compound according to Claim 1 having the formula:

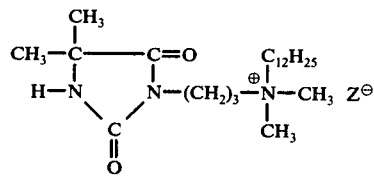

wherein Z is a physiologically acceptable anion.

7. A compound according to Claim 6 having the formula:

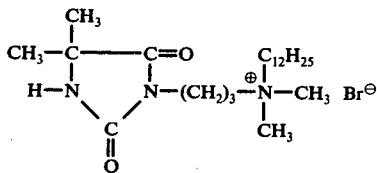

8. A broad spectrum fungicidal and bactericidal composition containing as an active ingredient a fungicidally and bactericidally effective amount of a compound according to claim 6, and a carrier for the active ingredient comprising an inert solid diluent or an inert liquid diluent.

9. A fungicidal and bactericidal composition according to claim 8 containing from about 0.0025 to about 10.0%, by weight, of the active ingredient.

10. A fungicidal composition according to claim 9 containing from about 0.0025 to about 0.1%, by weight, of the active ingredient.

11. A method of combating undesired bactericidal and fungicidal infestations in cosmetic compositions which comprises incorporating therein a fungicidally and bactericidally effective amount of a compound according to claim 6.

12. A method of protecting skin from bacteria and fungi which comprises applying to the skin a bactericidally and fungicidally effective amount of a compound according to claim 6.

13. A method of combating undesired fungicidal and bactericidal infestation in skin wounds which comprises applying to the locus of the skin wound a fungicidally and bactericidally effective amount of a compound as defined in claim 6.

* * * * *